United States Patent [19]

Butler

[11] 4,372,966

[45] Feb. 8, 1983

[54] USE OF DIHYDRO-1H-PYRROLIZINE-3,5(2H,6H)-DIONE AS A COGNITION ACTIVATOR

[75] Inventor: Donald E. Butler, Ann Arbor, Mich.

[73] Assignee: Warner-Lambert Company, Morris Plains, N.J.

[21] Appl. No.: 290,114

[22] Filed: Aug. 7, 1981

Related U.S. Application Data

[63] Continuation of Ser. No. 186,945, Sep. 15, 1980.

[51] Int. Cl.³ .................................................. A61K 31/40
[52] U.S. Cl. ............................................................ 424/274
[58] Field of Search ............................................. 424/274

*Primary Examiner*—Stanley J. Friedman
*Attorney, Agent, or Firm*—Stephen I. Miller

[57] ABSTRACT

Dihydro-1H-pyrrolizine-3,5(2H,6H)-dione is a cognition activator. The compound and compositions thereof are useful in the treatment of senility, in enhancing memory and reversing amnesia caused by electroconvulsive shock.

15 Claims, No Drawings

USE OF DIHYDRO-1H-PYRROLIZINE-3,5(2H,6H)-DIONE AS A COGNITION ACTIVATOR

CROSS REFERENCE TO RELATED APPLICATION

This application is a continuation in part of my copending application Ser. No. 186,945, filed Sept. 15, 1980.

SUMMARY AND DETAILED DESCRIPTION

The present invention relates to the use of dihydro-1H-pyrrolizine-3,5(2H,6H)-dione also known as 3,5-dioxopyrrolizidine and as 1-azabicyclo[3,3,0]octane-2,8-dione, as a cognition activator. More specifically it is useful in the treatment of patients suffering from senility and is also useful for enhancing memory and in the treatment of induced amnesia. Included in the present invention is the use as cognition activators of pharmaceutically acceptable compositions and the solvates and hydrates of said compound.

The compound is prepared by modification of the method described by N. J. Leonard, et al. in J. Amer. Chem. Soc., 69, 690–692 (1947). The modified synthesis is described herein. The starting compound is prepared by the method described in U.S. Pat. No. 2,390,918.

Dihydro-1H-pyrrolizine-3,5(2H,6H)-dione may exist in anhydrous form as well as in solvated, including hydrated, forms. In general, the hydrated forms and the solvated forms with pharmaceutically acceptable solvents are equivalent to the anhydrous or unsolvated form for the purposes of the invention.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeniously therein as by stirring. The molten homogenious mixture is then poured into convenient sized molds, allowed to cool and thereby to solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solublizing agents and the like. The liquid utilized for preparing the liquid form preparation may be water, isotonic water, ethanol, glycerine, propylene glycol and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from 1 mg to 100 mg according to the particular application and the potency of the active ingredient. The compositions can, if desired, also contain other therapeutic agents.

In therapeutic use as cognition activators, the mammalian dosage range for a 70 kg subject is from 1 to 1500 mg/kg of body weight per day or preferrably 25 to 750 mg/kg of body weight per day. The dosages, however, may be varied depending upon the requirements of the patient, the severity of the condition being treated and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The effectiveness of the aforementioned compound is determined by the test designed to show the compound's ability to reverse amnesia produced by electroconvulsive shock. The test is fully described in U.S. Pat. No. 4,145,347, issued Mar. 20, 1979 and is herein incorporated by reference. The only difference being that the test compound in the present instance was administered orally.

The following criteria is used in interpreting the percent of amnesia reversal scores: 40 percent or more (active=A) 25 to 39 percent (borderline=C) and 0 to 24 percent (inactive=N).

Table I below reports the percent of amensia reversal of orally administered dihydro-1H-pyrrolizine-3,5(2H,6H)-dione.

TABLE I

| Dose mg/kg | 0.63 | 1.25 | 2.50 | 5.00 | 20.00 | 40.00 | 80.00 | 160.00 | 320.00 |
|---|---|---|---|---|---|---|---|---|---|
| % Reversal | 73 | 27 | 25 | 69 | 31 | 92 | 63 | 62 | 85 |
| Rating | A | C | C | A | C | A | A | A | A |

The utility of dihydro-1H-pyrrolizine-3,5(2H,6H)-dione in enhancing memory is demonstrated by the Rodent Delayed Alternation test.

This test assesses the effects of drugs upon the performance of a short-term memory task in test-sophisticated rodents. The behavioral task employed is delayed spatial alternation using discrete trial procedures in a free operant setting. This task requires the animal to remember from one trial to the next which of two alternative levers was selected on the previous trial. The correct choice on the subsequent trial is always the alternate (or opposite) of that made on the previous trail. By controlling the delay between trials (inter-trial interval or ITI), it is possible to measure short-term memory at various times after the to-be-remembered event has occurred.

PRELIMINARY TRAINING

Since the delayed alternation task is somewhat complex, rather extensive training is required before drug testing may begin. Rats are first trained to bar press for food reinforcement while being maintained on a 22-hour food deprivation schedule. Initially, a single bar press delivers the 45 mg food pellet reward (continuous reinforcement or CRF schedule). The number of presses required is gradually increased until the animal must respond 8 times (FR 8 schedule) to obtain a single pellet. The animals are then trained to alternate their responses between the two available levers. A cue lamp above the correct lever signals the correct manipulation. Once the animal is alternating under the FR-8 requirement the light cue is removed (lamps are lit above both levers) and the animal must remember which is the correct side on the basis of the lever used on the previous trial. When the animal can alternate successfully with modest delays (10-20 sec) between trials—generally after 4-6 weeks of training—drug testing begins.

Drug Testing

A drug test consists of two consecutive experimental sessions. The only difference between the two sessions is the oral dosing of the drug on the second test day. The first session is an undrugged control session to compare with the drug performance of the second session.

An experimental session consists of the following procedures: One-half hour prior to being placed in the experimental chamber, the animal is removed from the home cage in the colony room and dosed orally (volume 1 cc/kg) with the experimental or control solution. (Animals are housed 1-3/cage in the colony and are maintained on 12—12 light/dark cycle with free access to water in the home cage and experimental chamber.) The animal is then placed in a retaining cage for the duration of the drug absorption period when the test begins.

Thirty min after injection, the animal is placed into the experimental chamber and the test session is initiated by a response from the experimenter. While in the operant chamber (Skinner box), the animal is presented with a series of trials, each trial separated from the previous by an inter-trial interval (ITI) whose duration is controlled by the experimental apparatus. A trial is signalled by lighted lamps above both levers. Between trials the lamps are dark. The correct lever is always the alternate of that chosen (by meeting the FR-8 requirement) on the previous trial. Incorrect responses—those made on the same lever as that of the previous trial—are counted but do not influence the trial outcome unless the FR-8 requirement is met. If the animal responds correctly 8 times (FR-8), the food reinforcement is delivered and the trial is terminated. If the animal responds 8 times to the incorrect lever, a buzzer is sounded for 1 sec and the trial is terminated. A new trial begins after the new ITI value has elapsed. The minimum duration of the ITI is determined by randomly choosing one of four values selected by the experimenter. The randomization procedure has the single constraint that for each block of 20 trials each of the 4 ITI values be selected an equal number of times (5). The test session continues either for a specified period of time—generally 1-2 hours—or until a certain number of trials or reinforcements has occurred (around 100 trials).

The number of reinforcements that an animal can earn per unit of time is held somewhat constant by rewarding the animal with multiple pellets after long delay intervals. Thus, if an animal must wait an average of 30 sec to earn one pellet (ITI=30 sec), ITI's of 60 sec. and 90 sec will be rewarded with 2 and 3 pellets respectively, if the animal responds correctly. The shorter intervals are, therefore, rewarded with a single pellet. The longer two delays, ranked according to length, are rewarded with two and three pellets, respectively.

Tests are evaluated on both qualitative and quantitative measures. For the qualitative evaluation, the number of animals showing improvement in performance on the drug day as compared with the control day is computed. The quantitative evaluation is obtained by computing the amount of improvement at each of the delay intervals on drugged vs undrugged days. Since the quantitative evaluation is intended to provide an estimate of the magnitude of the drug's enhancing effect, it is made only for dosages which show activity in the qualitative evaluation.

Thus, particular dosage of drug may receive two ratings: the first related to the reliability of the drug facilitation. The ratings on this measure are listed below:

| PERCENT OF ANIMALS SHOWING IMPROVEMENT | |
|---|---|
| Scores | Ratings |
| 75% and up | A - Active |
| 65%–74% | C - Borderline |
| 25%–64% | N - Inactive |
| 24% and less | U - Disruptive |

The dosages showing activity in the qualitative analysis (rating of A or C above) are further analyzed to estimate the extent of the facilitating effects.

This quantitative rating is determined by dividing the difference between drug and control scores at each of the delay intervals by the control score as follows:

$$\% \text{ improvement} = \frac{\text{drug score} - \text{control score}}{\text{control score}} \times 100$$

The mean amount of improvement across all delay intervals is then rated according to the following scale:

| AMOUNT OF MEMORY ENHANCEMENT | |
|---|---|
| % Improvement | Rating |
| 20% or more | B - Marked Activity |
| 10%–19% | C - Moderate Activity |
| less than 10% | D - Slight activity |

This test is duplicated to insure that the results are real. Table II and III below report typical memory enhancement results caused by dihydro-1H-pyrrolizine-3,5(2H,6H)-dione.

PREPARATION OF DIHYDRO-1H-PYRROLIZINE-3,5(2H,6H)-DIONE

A two gallon 316 stainless steel stirred autoclave is charged with 744 g (3.2 moles) γ-nitrodimethylpimelate containing 15 g 20% Palladium on carbon. Reagent grade methanol (3.78 l) is added and the reactor pressurized to 50 psig with hydrogen. The stirrer is started, and a smooth uptake of hydrogen is observed over ca. five hours, with a maximum temperature of 43° C. generated. The reduction mixture is withdrawn after hydrogen uptake ceases, and the catalyst filtered off on a ½" bed of Super-Cel on a medium porosity sintered glass funnel. The clear, water-white solution is concentrated on a 10 l rotary evaporator at 45° C. (12 mm). When no more distillate is observed, the temperature of the bath is raised to 100° C. to remove the balance of volatiles and promote ring closure of any amino ester present. A yield of 553 g of a viscous dark-yellow oil is obtained.

This mixture of pyrrolidin-2-one-5-(β-carbomethoxyethyl) and pyrrolidin-2-one-5-propanoic acid is dissolved in 600 ml methanol in a 5 l four-necked flask fitted with mechanical stirrer, y-tube, condenser, and thermometer. To the stirred solution is added 400 ml deionized water followed by 296 g (3.70 mole) 50% sodium hydroxide solution. Water (200 ml) is used as a rinse, and the final temperature is 65° C. The tan solution is heated at reflux overnight.

After cooling, the hydrolysis mixture is drawn directly into a 10 l rotary evaporator and the methanol stripped at 45° C. (12 mm). A solution of 330 ml (3.8 mole) concentrated HCl in 300 ml deionized water is slowly drawn into the rotary evaporator. The balance of volatile material is removed at 60° C. (12 mm). The thick, pasty residue of pyrrolidin-2-one-5-propanoic acid is slowly treated with 500 ml acetic anhydride (Caution) with stirring and scraping to render the material transferable. The resulting slurry is poured into a 5 l, three-necked flask fitted with stirrer and condenser

TABLE II

| | | Qualitative Evaluation | | Quantitative Evaluation | | | | | |
|---|---|---|---|---|---|---|---|---|---|
| | | | | | Percent Improvement | | | | |
| | | No. of | Better | | | at Delay Time, Sec. | | | |
| Dose | Units | Rating | Animals | Score | Rating | Total | 0–30 | 30–60 | 60–90 | 90–120 |
| 80.00 | M/K | A | 17 | 76% | D | 6% | 5% | 5% | | |
| 40.00 | M/K | N | 13 | 46% | | | | | 7% | 4% |
| 20.00 | M/K | A | 15 | 80% | D | 4% | 3% | 1% | | |
| 10.00 | M/K | C | 15 | 73% | D | 3% | 1% | 1% | 4% | 8% |
| 5.00 | M/K | N | 16 | 63% | D | 0% | 0% | 1% | 0% | 11% |
| | | | | | | | | | 2% | 0% |

Rating: A—Active (> or 75%); C—Borderline (65%–74%); N—Inactive (25–64%); D—Disruptive (<25%)
Quantitative Rating: B—Marked Activity (> or 20%); C—Moderate Activity (10–19%); D—Slight activity (<10%)

(Drierite protected) along with an additional 1000 ml

TABLE III

| | | | Qualitative Evaluation | | Quantitative Evaluation | | | | |
|---|---|---|---|---|---|---|---|---|---|
| | | | | | | Percent Improvement | | | |
| | | | No. of | Better | | | at Delay Time, Sec. | | |
| Dose | Units | Rating | Animals | Score | Rating | Total | 0–30 | 30–60 | 60–90 | 90–120 |
| 80.00 | M/K | C | 14 | 71% | D | 6% | 3% | 2% | 3% | 16% |
| 40.00 | M/K | A | 15 | 80% | D | 6% | 0% | 1% | 10% | 8% |
| 20.00 | M/K | A | 16 | 75% | D | 4% | 0% | 1% | 9% | 0% |
| 10.00 | M/K | N | 16 | 38% | | | | | | |
| 5.00 | M/K | N | 15 | 60% | | | | | | |

Rating: A—Active (> or 75%); C—Borderline (65–74%); N—Inactive (25–64%); O—Disruptive (<25%)
Quantitative Rating: B—Marked Activity (> or 20%); C—Moderate Activity (10%)

acetic anhydride. The temperature increases to 45° C. during the addition. The tan suspension is heated at 95° C. overnight, with stirring.

The dark suspension is then cooled to 60° C. and the sodium chloride filtered off through a medium porosity sintered glass funnel. The filter cake is washed with 200 ml hot acetic anhydride and the filtrate stripped of volatiles on a rotary evaporator at 60° C. (12 mm). Toluene (1 liter) is added to the residue, then 150 ml stripped out on a rotary evaporator at 45° C. (12 mm). The resulting dark solution is ice-bath chilled to 5° C. and a crop of solid collected. The filter cake is well pressed to clear all dark supernatant liquid, then washed with 500 ml ethyl ether. The tan solid is dried over night at 50° C. in vacuo. The yield is 211 g, melting at 178°–182° C., representing a 48% overall yield including the reduction, hydrolysis, and ring closure steps.

The crude product (211 g) is dissolved in 2.5 l of isopropanol on the steam bath. Fifteen grams Darco G-60 is added and the mixture filtered through a heated sintered glass funnel containing a 178 " layer of Super-Cel under a slight vacuum. The filtrate is ice-bath cooled to 5° C., and a crop of solid collected. The crystals are washed on the funnel with 200 ml 5° C. isopropanol before drying at 50° C. in vacuo. The yield is 192 g (91% recovery) (43.7% overall) mp 180°–183° C. (open capillary).

PREPARATION OF DIHYDRO-1H-PYRROLIZINE-3,5(2H,6H)-DIONE

A solution of 136 g of gamma-nitropimelic acid dimethyl ester in 500 ml of methanol is hydrogenated at approximately 3780 psi using 15 g of Raney Nickel as catalyst. The resulting slurry is filtered to remove the catalyst and the filtrate is concentrated at reduced pressure to yield crude 5-oxo-2-pyrrolidinepropanoic acid methyl ester. The 5-oxo-2-pyrrolidinepropanoic acid methyl ester is dissolved in 100 ml of methanol and 100 ml of water and is treated with 94 g of 50% sodium hydroxide solution. The reaction mixture is stirred and is heated to 98° C. with distillation of methanol. The solution is cooled, neutralized with 151 ml of concentrated hydrochloric acid and concentrated at reduced pressure. The residue containing 5-oxo-2-pyrrolidine-propanoic acid is heated at 98°–100° C. for 24 hours with 200 ml of acetic anhydride. The sodium chloride is removed by filtration after the acetic anhydride reaction. The filtrate is then concentrated at reduced pressure and 200 ml of toluene is added and concentration is repeated. The dihydro-1H-pyrrolizine-3,5-(2H,6H)-dione crystallizes and is isolated by filtration. The product is best purified by sublimation at 100° C. and 0.1 mm Hg or by recrystallization from ethanol to give melting point of 179°–182° C.

The invention is further illustrated by the following non-limiting Examples.

EXAMPLE 1

| Ingredient | Quantity |
|---|---|
| Dihydro-1H—pyrrolizine-3,5(2H,6H)-dione | 150 g |
| Lactose | 1124 g |
| Corn Starch | 39 g |
| Hydroxypropylcellulose | 30 g |
| Magnesium stearate | 7 g |
| Ethanol-water 50:50 | q.s. |

The dihydro-1H-pyrrolizine-3,5(2H,6H)-dione, lactose and hydroxypropylcellulose are blended and granulated with 50:50 ethanol-water. The wet granulation is screened, dried, and rescreened. The resulting dried granulation is blended with magnesium stearate and the corn starch and the mixture is compressed into 225 mg tablets using a 11/32 inch standard concave punch. Yield equals approximately 6000 tablets each containing 25.0 mg of dihydro-1H-pyrrolizine-3,5(2H,6H)-dione.

EXAMPLE 2

| Ingredient | Quantity |
|---|---|
| Dihydro-1H—pyrrolizine-3,5(2H,6H)-dione | 15 g |
| Lactose | 1259 g |
| Corn Starch | 39 g |
| Hydroxypropylcellulose | 30 g |
| Magnesium stearate | 7 g |
| Ethanol-water 50:50 | q.s. |

The dihydro-1H-pyrrolizine-3,5(2H,6H)-dione, lactose and hydroxypropylcellulose are blended and granulated with 50:50 ethanol-water. The wet granulation is screened, dried, and rescreened. The resulting dried granulation is blended with magnesium stearate and the corn starch and the mixture is compressed into 225 mg tablets using a 11/32 inch standard concave punch. Yield equals approximately 6000 tablets each containing 2.5 mg of dihydro-1H-pyrrolizine-3,5(2H,6H)-dione.

EXAMPLE 3

| Ingredient | Quantity |
|---|---|
| Dihydro-1H—pyrrolizine-3,5(2H,6H)-dione | 6 g |
| Lactose | 1268 g |
| Corn Starch | 39 g |
| Hydroxypropylcellulose | 30 g |
| Magnesium stearate | 7 g |
| Ethanol-water 50:50 | q.s. |

The dihydro-1H-pyrrolizine-3,5(2H,6H)-dione, lactose and hydroxypropylcellulose are blended and granulated with 50:50 ethanol-water. The wet granulation is screened, dried, and rescreened. The resulting dried granulation is blended with magnesium stearate and the corn starch and the mixture is compressed into 225 mg tablets using 11/32 inch standard concave punch. Yield equals approximately 6000 tablets each containing 1.0 mg of dihydro-1H-pyrrolizine-3,5(2H,6H)-dione.

EXAMPLE 4

| Ingredient | Quantity |
|---|---|
| Dihydro-1H—pyrrolizine-3,5(2H,6H)-dione | 300 g |
| Lactose | 974 g |
| Corn Starch | 39 g |
| Hydroxypropylcellulose | 30 g |
| Magnesium stearate | 7 g |
| Ethanol-water 50:50 | q.s. |

The Dihydro-1H-pyrrolizine-3,5(2H,6H)-dione, lactose and hydroxypropylcellulose are blended and granulated with 50:50 ethanol-water. The wet granulation is screened, dried, and rescreened. The resulting dried granulation is blended with magnesium stearate and the corn starch and the mixture is compressed into 225 mg tablets using a 11/32 inch standard concave punch. Yield equals approximately 6000 tablets each containing 50.0 mg of Dihydro-1H-pyrrolizine-3,5(2H,6H)-dione.

EXAMPLE 5

| Ingredient | Quantity |
| --- | --- |
| Dihydro-1H—pyrrolizine-3,5(2H,6H)-dione | 250 g |
| Lactose | 1723 g |
| Magnesium stearate | 27 g |

The mixture is blended and filled into No. 4 hard gelatin capsules, filling each capsule with 200 mg of the powder mixture. Yield equals approximately 10,000 capsules each containing 25.0 mg of dihydro-1H-pyrrolizine-3,5(2H,6H)-dione.

EXAMPLE 6

| Ingredient | Quantity |
| --- | --- |
| Dihydro-1H—pyrrolizine-3,5(2H,6H)-dione | 25 g |
| Lactose | 1948 g |
| Magnesium stearate | 27 g |

The mixture is blended and filled into No. 4 hard gelatin capsules, filling each capsule with 200 mg of the powder mixture. Yield equals approximately 10,000 capsules each containing 2.5 mg of dihydro-1H-pyrrolizine-3,5(2H,6H)-dione.

EXAMPLE 7

| Ingredient | Quantity |
| --- | --- |
| Dihydro-1H—pyrrolizine-3,5(2H,6H)-dione | 10 g |
| Lactose | 1963 g |
| Magnesium stearate | 27 g |

The mixture is blended and filled into No. 4 hard gelatin capsules, filling each capsule with 200 mg of the powder mixture. Yield equals approximately 10,000 capsules each containing 1.0 mg of dihydro-1H-pyrrolizine-3,5(2H,6H)-dione.

EXAMPLE 8

| Ingredient | Quantity |
| --- | --- |
| Dihydro-1H—pyrrolizine-3,5(2H,6H)-dione | 500 g |
| Lactose | 1473 g |
| Magnesium stearate | 27 g |

The mixture is blended and filled into No. 4 hard gelatin capsules, filling each capsule with 200 mg of the powder mixture. Yield equals approximately 10,000 capsules each containing 50.0 mg of dihydro-1H-pyrrolizine-3,5(2H,6H)-dione.

EXAMPLE 9

| Ingredient | Quantity |
| --- | --- |
| Dihydro-1H—pyrrolizine-3,5(2H,6H)-dione | 1.0 mg |
| Phemerol Chloride Recrystallized | 0.1 mg |
| Water for Injection USP | q.s. to 1.0 ml |

The dihydro-1H-pyrrolizine-3,5(2H,6H)-dione is mixed with about two thirds of the required volume of Water for Injection USP followed by the addition of sufficient Water for Injection to reach the desired volume. After mixing, the solution is sterilized by membrane filtration (a 0.22 micron Millipore filter membrane represents a suitable filter). The desired quantity of above prepared solution is filled into approximate size multiple dose vials suitable for injection preparations and stopper with gum rubber or suitable rubber closures and sealed with aluminum ferrules. The preparation may also be filled into suitable size single dose glass ampoules and sealed.

Using the above procedure, solutions containing 1.0, 2.5, 5.0 or 10.0 mg/ml of dihydro-1H-pyrrolizine-3,5(2H,6H)-dione may be prepared.

EXAMPLE 10

Suppository Formulation of Dihydro-1H-pyrrolizine-3,5(2H,6H)-dione

| Ingredient | Quantity |
| --- | --- |
| Dihydro-1H—pyrrolizine-3,5(2H,6H)-dione | 500 g |
| Carrier (mixed fatty acid glycerides) | 1,500 g |

Fifteen hundred grams of the carrier are heated until melted. The 500 grams of dihydro-1H-pyrrolizine-3,5(2H,6H)-dione are added and mixed until uniform.

The molten mixture is poured into standard two gram molds and molded at 34° C. The yield equals approximately 1000 2 gram-suppositories each containing 500 mg of dihydro-1H-pyrrolizine-3,5(2H,6H)-dione.

EXAMPLE 11

Suppository Formulation of Dihydro-1H-pyrrolizine-3,5(2H,6H)-dione

| Ingredient | Quantity |
| --- | --- |
| Dihydro-1H—pyrrolizine-3,5(2H,6H)-dione | 30 g |
| Carrier (mixed fatty acid glycerides) | 1,970 g |

One thousand nine hundred and seventy grams of the carrier are heated until melted. The 30 grams of the dihydro-1H-pyrrolizine-3,5(2H,6H)-dione are added and mixed until uniform. The molten mixture is poured into standard two gram molds and molded at 34° C. The yield equals approximately 1000 2 gram-suppositories each containing 30 mg of dihydro-1H-pyrrolizine-3,5(2H,6H)-dione.

EXAMPLE 12

Suspension Formulation of Dihydro-1H-pyrrolizine-3,5(2H,6H)-dione

| Ingredient | Quantity |
| --- | --- |
| Dihydro-1H—pyrrolizine-3,5(2H,6H)-dione | 200 g |
| Sodium Saccharin | 50 g |
| Trihydroxystearin | 100 g |
| Propylparaben | 10 g |
| Imitation Cherry Flavor | 20 g |
| Vehicle (caprylic/capric triglycerides) | q.s. to 1000 ml |

The 10 grams of propylparaben are added to 400 grams of the vehicle and the mixture is heated to 55° C. until solution is complete. The 100 grams of trihydroxystearin are added and the mixture is homogenized until the temperature reaches 45° C. The mixture is cooled to room temperature and 200 grams of dihydro-1H-pyrrolizine-3,5(2H,6H)-dione, 20 grams of imitation cherry flavor and 50 grams of sodium saccharin are added. The suspension is diluted to 1000 ml with the vehicle. This yields a suspension containing 1 gram of dihydro-1H-pyrrolizine-3,5(2H,6H)-dione per 5 ml of suspension.

EXAMPLE 13

Suspension Formulation of Dihydro-1H-pyrrolizine-3,5(2H,6H)-dione

| Ingredient | Quantity |
| --- | --- |
| Dihydro-1H-pyrrolizine-3,5(2H,6H)-dione | 20 g |
| Sodium Saccharin | 25 g |
| Trihydroxystearin | 100 g |
| Propylparaben | 10 g |
| Imitation Cherry Flavor | 20 g |
| Vehicle (caprylic/capric triglycerides) | q.s. to 1000 ml |

The 10 grams of propylparaben are added to 400 grams of the vehicle and the mixture is heated to 55° C. until solution is complete. The 100 grams of trihydroxystearin are added and the mixture is homogenized until the temperature reaches 45° C. The mixture is cooled to room temperature and 20.0 grams of dihydro-1H-pyrrolizine-3,5(2H,6H)-dione, 25 grams of sodium saccharin and 20 grams of imitation cherry flavor are added. The suspension is diluted to 1000 ml with the vehicle. This yields a suspension containing 100 mg of dihydro-1H-pyrrolizine-3,5(2H,6H)-dione per 5 ml of suspension.

EXAMPLE 14

Suspension Formulation of dihydro-1H-pyrrolizine-3,5(2H,6H)-dione

| Ingredient | Quantity |
| --- | --- |
| Dihydro-1H—pyrrolizine-3,5(2H,6H)-dione | 50 g |
| Sodium Saccharin | 50 g |
| Trihydroxystearin | 50 g |
| Propylparaben | 10 g |
| Imitation Cherry Flavor | 20 g |
| Vehicle (caprylic/capric triglycerides) | q.s. to 1000 ml |

The 10 grams of propylparaben are added to 400 g of the vehicle and the mixture is heated to 55° C. until solution is complete. The 50 grams of trihydroxystearin is added and the mixture is homogenized until the temperature reaches 45° C. The mixture is cooled to room temperature and 50 grams of dihydro-1H-pyrrolizine-3,5(2H,6H)-dione, 50 grams of sodium saccharin and 20 grams of imitation cherry flavor are added. The suspension is diluted to 1000 ml with the vehicle. This yields a suspension containing 250 mg of dihydro-1H-pyrrolizine-3,5(2H,6H)-dione per 5 ml of suspension.

EXAMPLE 15

Syrup for Reconstitution Formulation of Dihydro-1H-pyrrolizine-3,5(2H,6H)-dione

| Ingredient | Quantity |
| --- | --- |
| Dihydro-1H—pyrrolizine-3,5(2H,6H)-dione | 100 g |
| Sugar Granulated (Bottlers grade) | 400 g |
| Artificial Peppermint Flavor Water Soluble Spray dried | 10 g |
| Water | q.s. to 1000 ml at time of dispensing |

Dry blend the 100 grams of dihydro-1H-pyrrolizine-3,5(2H,6H)-dione, 400 grams of granulated sugar (bottlers grade) and 10 grams of artificial peppermint flavor. Add water q.s. to 1000 ml at time of dispensing and shake until dissolution. Refrigerated storage and use within one week is recommended. This syrup contains 500 mg of dihydro-1H-pyrrolizine-3,5(2H,6H)-dione per 5 ml of syrup.

EXAMPLE 16

Syrup for Reconstitution Formulation of Dihydro-1H-pyrrolizine-3,5(2H,6H)-dione

| Ingredient | Quantity |
| --- | --- |
| Dihydro-1H—pyrrolizine-3,5(2H,6H)-dione | 50 g |
| Sugar granulated (Bottlers grade) | 400 g |
| Artificial Peppermint Flavor Water Soluble Spray dried | 10 g |
| Water | q.s. to 1000 ml at time of dispensing |

Dry blend the 50 grams of dihydro-1H-pyrrolizine-3,5(2H,6H)-dione, 400 grams of granulated sugar (bottlers grade) and 10 grams of artificial peppermint flavor. Add water q.s. to 1000 ml at time of dispensing and shake until dissolution. Refrigerated dione, 400 grams of granulated sugar (bottlers grade) and 10 grams of artificial peppermint flavor. Add water q.s. to 1000 ml at time of dispensing and shake until dissolution. Refrigerated storage and use within one week is recommended. This syrup contains 250.0 mg of dihydro-1H-pyrrolizine-3,5(2H,6H)-dione per 5 ml of syrup.

EXAMPLE 17

Syrup for Reconstitution Formulation of Dihydro-1H-pyrrolizine-3,5(2H,6H)-dione

| Ingredient | Quantity |
| --- | --- |
| Dihydro-1H—pyrrolizine-3,5(2H,6H)-dione | 25 g |
| Sugar Granulated (Bottlers grade) | 400 g |
| Artificial Peppermint Flavor Water Soluble Spray dried | 10 g |
| Water | q.s. to 1000 ml at time of dispensing |

Dry blend the 25 grams of dihydro-1H-pyrrolizine-3,5(2H,6H)-dione, 400 grams of granulated sugar (bottlers grade) and 10 grams of artificial peppermint flavor. Add water q.s. to 1000 ml at time of dispensing and shake until dissolution. Refrigerated storage and use within one week is recommended. This syrup contains 125 mg of dihydro-1H-pyrrolizine-3,5(2H,6H)-dione per 5 ml of syrup.

I claim:

1. A pharmaceutical composition comprising a pharmaceutically effective amount of dihydro-1H-pyrrolizine-3,5(2H,6H)-dione in combination with a pharmaceutically acceptable carrier.

2. The composition defined in claim 1 which is in the form of a solid.

3. The composition defined in claim 1 which is in the form of a liquid.

4. The composition defined in claim 2 wherein said solid is converted to a liquid form composition such as a solution, suspension or emulsion before use.

5. The composition defined in claim 1 which is a liquid intended for oral use.

6. The composition defined in claim 4 which is intended for oral use.

7. The composition defined in claim 1 which is a liquid intended for parenteral use.

8. The composition defined in claim 4 which is intended for parenteral use.

9. A pharmaceutical composition in the form of a tablet, capsule or injectable useful for the treatment of senility, enhancing memory or reversing amnesia caused by electroconvulsive shock comprising an effective amount of dihydro-1H-pyrrolizine-3,5(2H,6H)-dione in a pharmaceutically acceptable carrier.

10. A method of treating senility, of enhancing memory or of reversing amnesia caused by electroconvulsive shock in humans which comprises administering to said human an effective amount of dihydro-1H-pyrrolizine-3,5(2H,6H)-dione.

11. A method for treating senility, for enhancing memory or for reversing amnesia caused by electroconvulsive shock in a mammal in need of said treatment, which method comprises administering to said mammal the pharmaceutical composition defined in claim 1, 2, 3, 4, 5, 6, 7 or 8.

12. The method defined in claim 11 which comprises administering the composition defined in claim 2.

13. The method defined in claim 11 which comprises administering the composition defined in claim 3.

14. The method defined in claim 11 which comprises administering the composition defined in claim 6.

15. The method defined in claim 11 which comprises administering the composition defined in claim 8.

* * * * *